US005659397A

United States Patent [19]
Miller et al.

[11] Patent Number: 5,659,397
[45] Date of Patent: Aug. 19, 1997

[54] METHOD AND APPARATUS FOR MEASURING TOTAL SPECULAR AND DIFFUSE OPTICAL PROPERTIES FROM THE SURFACE OF AN OBJECT

[75] Inventors: Edgar R. Miller; Richard J. Mell, both of Huntsville, Ala.

[73] Assignee: AZ Technology, Huntsville, Ala.

[21] Appl. No.: 488,996

[22] Filed: Jun. 8, 1995

[51] Int. Cl.$^6$ .............................. G01N 21/47; G01J 5/02
[52] U.S. Cl. .................... 356/446; 356/445; 250/341.8; 250/559.16
[58] Field of Search .................................. 356/445–446; 250/559.16, 341.8, 458.1

[56] References Cited

U.S. PATENT DOCUMENTS

| | | | |
|---|---|---|---|
| 3,010,358 | 11/1961 | Siegler | 356/244 |
| 3,504,983 | 4/1970 | Richmond et al. | |
| 3,874,799 | 4/1975 | Isaacs et al. | 356/236 |
| 4,177,383 | 12/1979 | Knight. | |
| 4,188,542 | 2/1980 | Hogg et al. | 250/458.1 |
| 4,188,543 | 2/1980 | Brunsting et al. | 356/339 |
| 4,360,275 | 11/1982 | Louderback | 356/446 |
| 4,487,504 | 12/1984 | Goldsmith | 356/447 |
| 4,578,584 | 3/1986 | Baumann et al. | |
| 4,630,276 | 12/1986 | Moran | 356/237 |
| 4,815,858 | 3/1989 | Snail | 356/446 |
| 4,925,305 | 5/1990 | Erickson | 356/243 |
| 4,988,205 | 1/1991 | Snail | 356/446 |
| 5,127,729 | 7/1992 | Oetliker et al. | 356/73 |
| 5,216,479 | 6/1993 | Dotan et al. | 356/446 |
| 5,313,542 | 5/1994 | Catonguay | 356/337 |

OTHER PUBLICATIONS

Smith, I.W., "Reflectometer for Laser Mirrors with Accuracy Better than $10^{-10}$," *Applied Optics*, vol. 17, No. 16, pp. 2476–2477 (Aug. 15, 1978).

Sales Brochure, Devices & Services Co., "Emissometer Model AE" (Dec. 1994).

Sales Brochure, Devices & Services Co., "Scaling Digital Voltmeter–RD1" (Dec. 1994).

*Primary Examiner*—Frank G. Font
*Assistant Examiner*—Jason D. Vierra Eisenberg
*Attorney, Agent, or Firm*—Needle & Rosenberg, P.C.

[57] ABSTRACT

A portable device for measuring total reflectance from the surface of an object by means of electromagnetic radiation has a housing defining an ellipsoidal chamber having a reflective interior surface, a first focus, an opposite second focus. The chamber defines a first aperture at the first focus, the first aperture being adapted for placement against the surface of the object so that a portion of the surface is in optical communication with the chamber. A light source illuminates the portion of the surface of the object through the first aperture with the electromagnetic radiation of a predetermined waveband, such as infrared. A means for measuring the radiation is disposed adjacent the second focus, so that when the first aperture is placed against the object, the electromagnetic radiation illuminates the object in an area adjacent the first focus. The reflected radiation, both specular and scattered, is directed by the interior reflective surface to the radiation measuring means. Disposed between the first focus and the second focus is a means for reflecting substantially all of the electromagnetic radiation from the source of focused radiation to the radiation measuring means, thereby providing a reference beam to the radiation measuring means. The ratio of the intensity of the light reflected off of the surface of the object to the intensity of the reference beam provides an indication of the absolute reflectance of the object. Also disclosed is a coating for transducing light into infrared light.

40 Claims, 5 Drawing Sheets

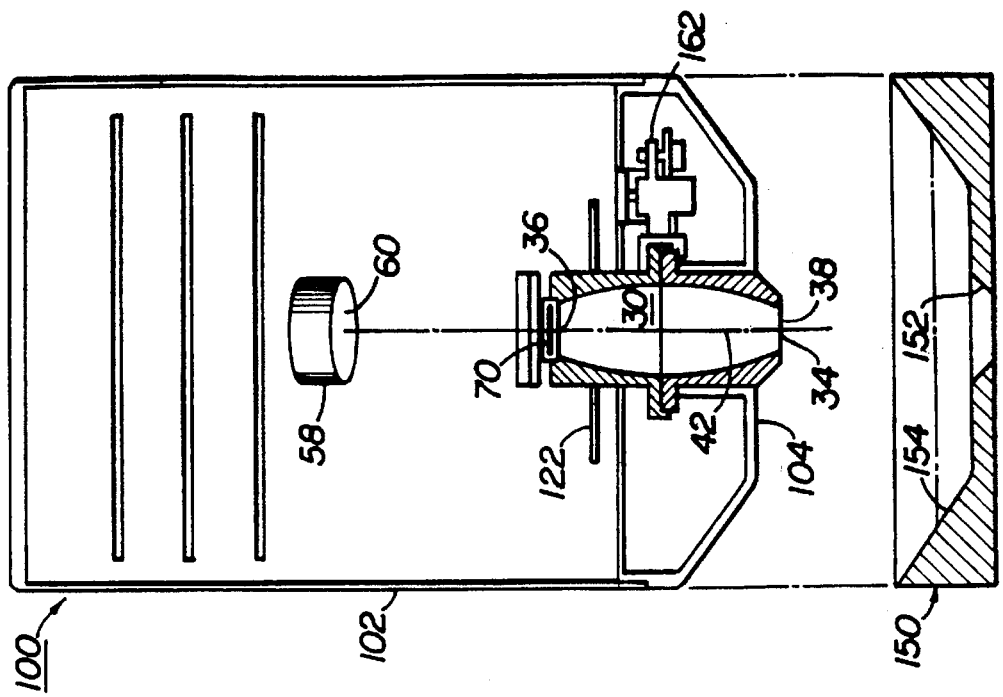
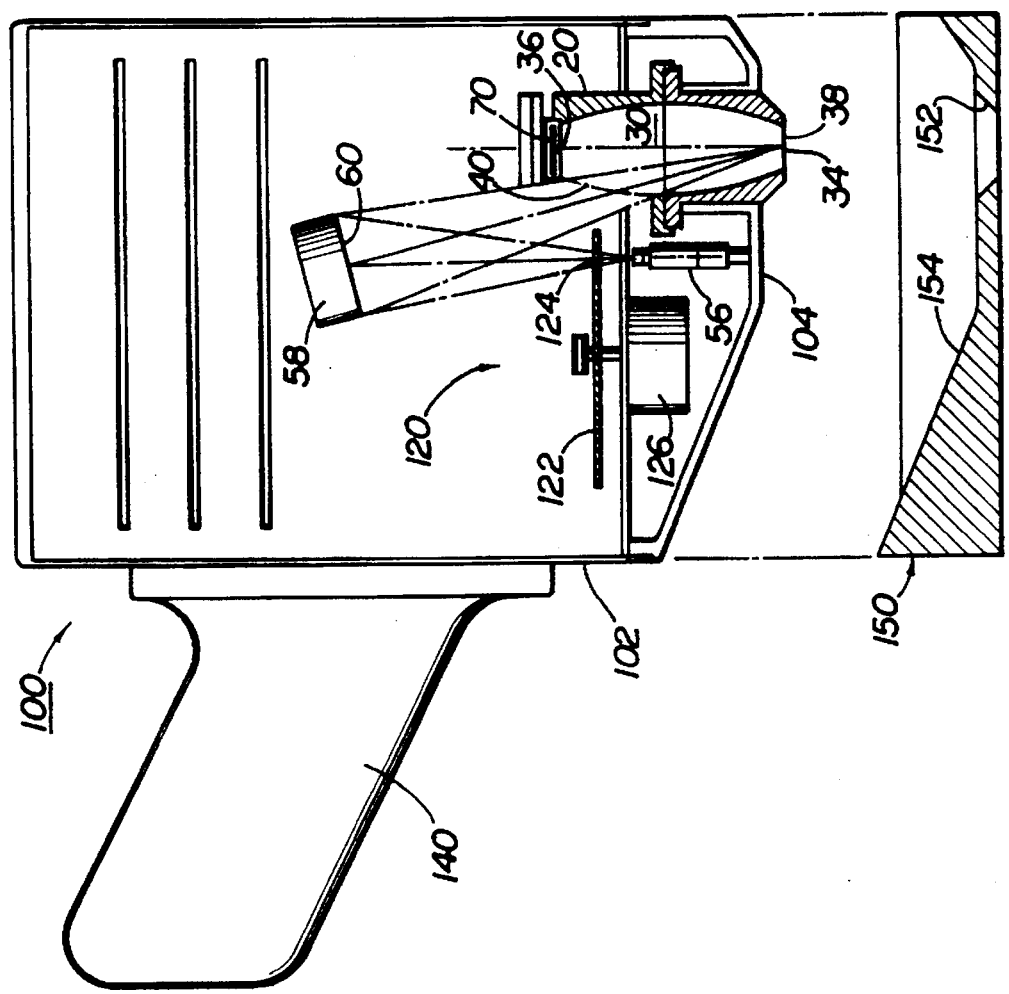

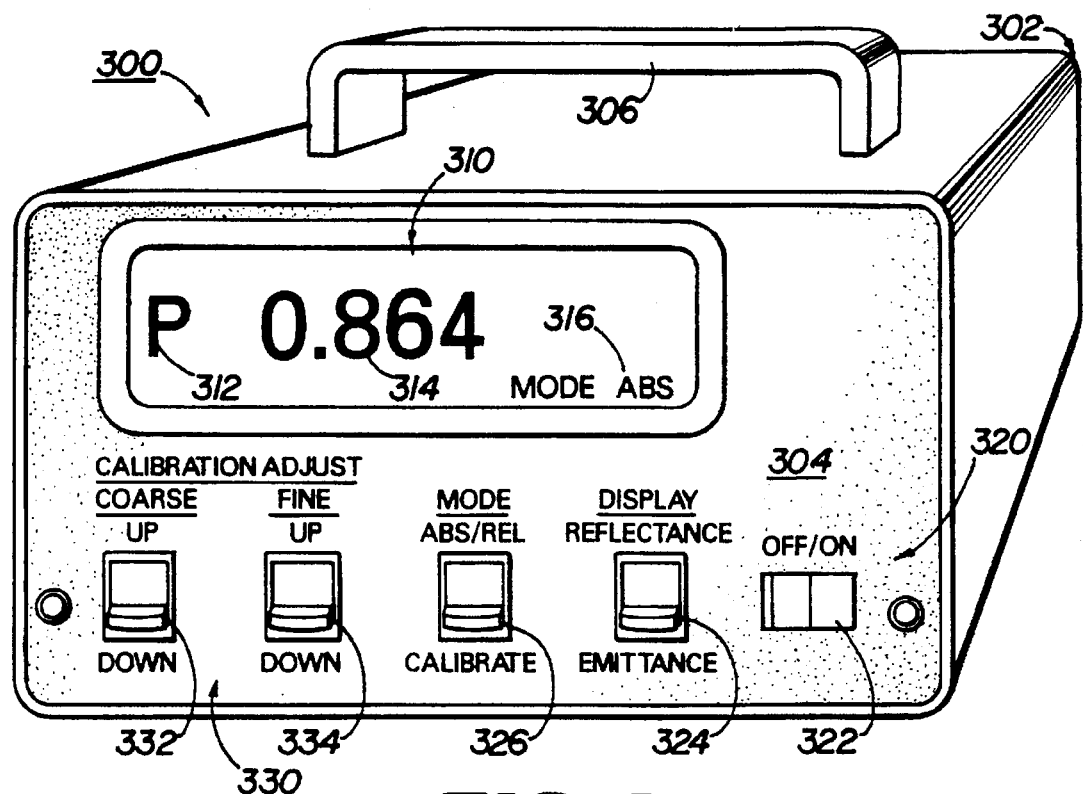
FIG 4
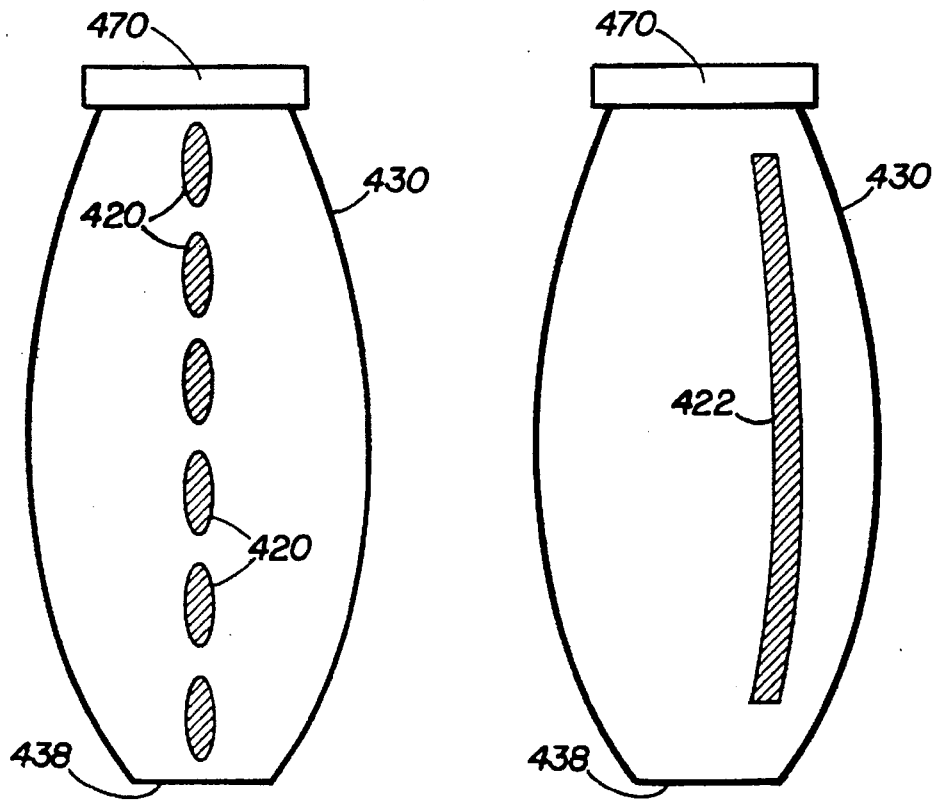
FIG 5A  FIG 5B

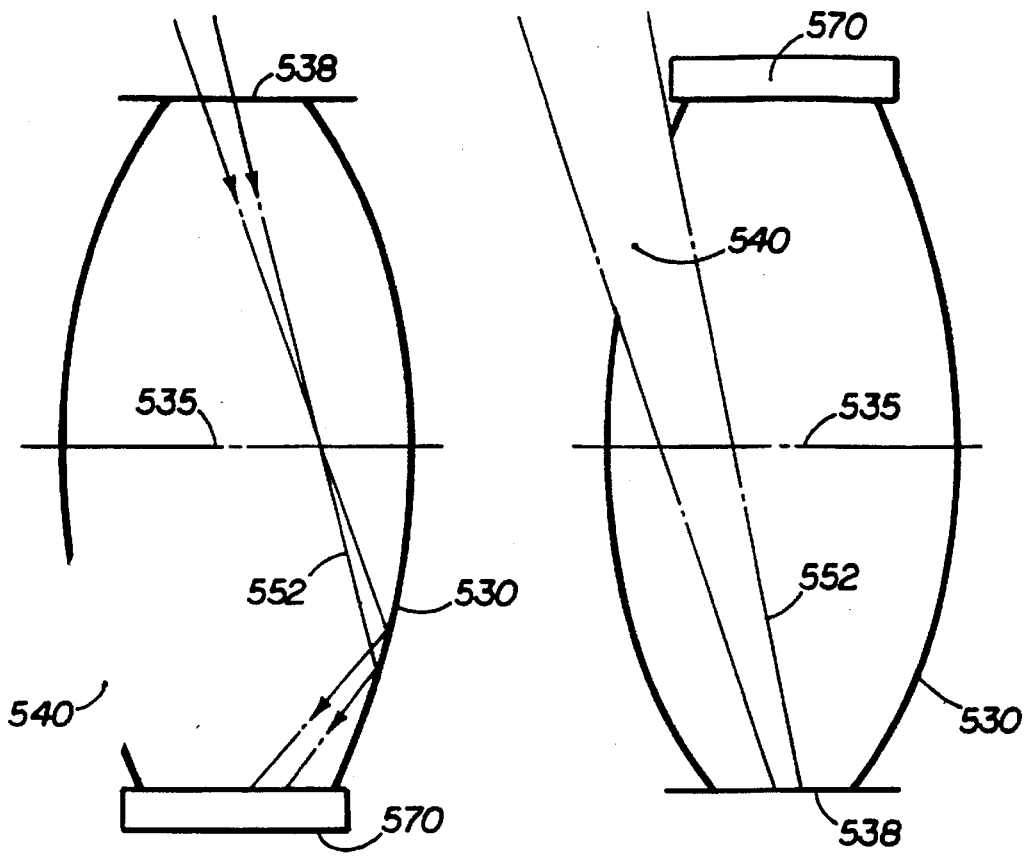
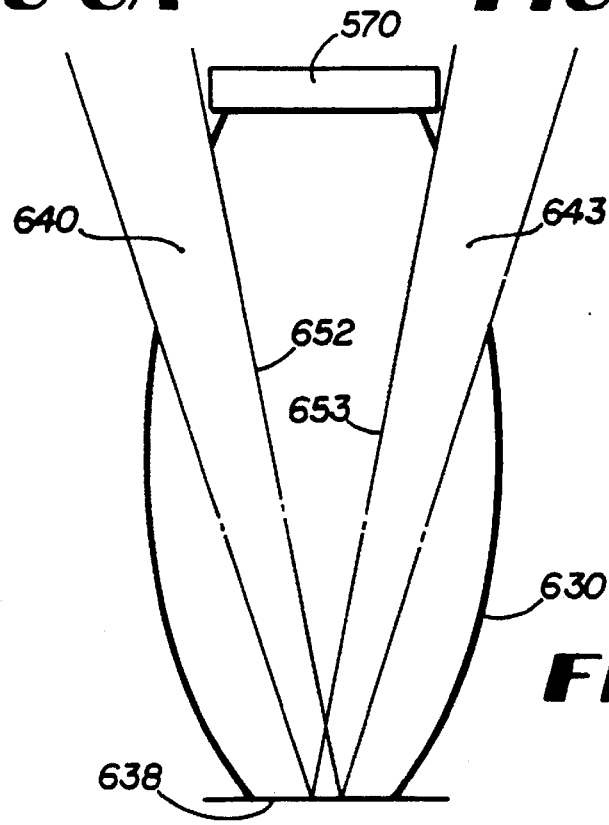

METHOD AND APPARATUS FOR MEASURING TOTAL SPECULAR AND DIFFUSE OPTICAL PROPERTIES FROM THE SURFACE OF AN OBJECT

BACKGROUND OF THE INVENTION

1. Field of the Invention

The present invention relates generally to measuring optical properties of a surface, and specifically to measuring total emittance from a surface.

2. Description of the Prior Art

Measuring surface optical properties (e.g., reflectance, transmittance and emittance) is vitally important in the aerospace industry. In order to control the surface temperatures of satellites, spacecraft and high-speed aircraft, airframe designers must be able to measure the heat absorbing and emittance properties of the surfaces they employ in their designs. Also, it is important to monitor the surface optical properties of reusable spacecraft (e.g., the space shuttle) to ensure continued safe operation. Such measurements are also important in solar energy applications and surface chemical analyses.

Currently, devices used to measure the surface reflectance of reusable space craft are not portable. To measure such reflectance, a technician must remove a sample from the spacecraft, patch the resulting hole, and mount the sample in a measurement device in a laboratory or more commonly, use a witness sample technique. Because of the complexity involved, such measurements are limited to only a few samples.

Several devices have been disclosed that measure some of the reflectance properties of surfaces. These include U.S. Pat. No. 4,360,275 issued to Louderback, which discloses a device for measuring total diffuse optical scattering from the surface of a sample, including a surface having extremely low scatter. A light beam from a laser is directed through an entrance hole in an ellipsoidal reflector onto the sample. A sample mounting means is used to position the sample so that the specularly reflected portion of the light beam is directed out of an exit hole located in the reflector diametrically opposite the entrance hole.

Prior to the measurement of scattering, the Louderback device must first be calibrated by measuring its output for a known amount of light scattering. This is accomplished by inserting in place of the sample a scattering sample having a known amount of scattering, such as a disk covered with barium sulfate ($BaSO_4$) having a 99% diffuse scattering. In addition, an optical filter having a known, low transmittance is inserted within the beam in between the output of the laser source and the entrance hole. The optical filter avoids exposing the sensitive photomultiplier tube to a high level of light that would saturate or even damage it. With the beam incident on the calibration sample, the voltage of the photomultiplier tube is adjusted so that the device reads the known transmittance of the optical filter directly.

U.S. Pat. No. 3,504,983 issued to Richmond et al. discloses a reflectometer in which a luminous flux is directed through an aperture in an ellipsoidal mirror to a specimen supported by a support means at the first focus of the ellipsoid. Light reflected off of the specimen is reflected off of the ellipsoidal mirror to a collecting sphere at the second focus of the ellipsoid. The collecting sphere directs the light to a detector.

U.S. Pat. No. 3,010,358 issued to Seigler discloses a radiation comparison system having off-axis ellipsoidal mirrors with a sample supported at one focus.

U.S. Pat. No. 4,177,383 issued to Knight discloses a device for treating a sheet material with radiation. An elliptical reflector directs light from an ultra-violet light source onto a surface being treated by the light.

U.S. Pat. No. 4,578,584 issued to Baumann et al. discloses a non-contact thermal imaging system in which an energy source is scanned across a sample supported by a pedestal. Suitable energy sources include electron beams, ion beams and laser beams. The scanned beam discontinuously heats discrete points of the surface of the sample. A thermal wave is generated on the surface of the sample and means are provided to image the two-dimensional area of the sample. A hemi-ellipsoidal reflector acts as a collector of infrared radiation with the sample placed at one focus and the detector placed at the opposite focus. The scanned beam passes through an aperture in the reflector.

U.S. Pat. No. 4,988,205 issued to Snail discloses a reflectometer in which the sample is placed at one focus of a hemi-ellipsoidal primary mirror. The sample is illuminated by a beam reflected into the cavity of the primary mirror. Light reflected off of the sample is directed, by the primary mirror, into a secondary mirror having an entrance aperture placed at the second focus of the primary mirror. The secondary mirror directs all entering light to a detector. In a second embodiment, the primary mirror is a dual paraboloid comprising two opposing mirror surfaces with the sample being placed at the focus of one paraboloid and the secondary mirror being placed at the focus of the second paraboloid.

U.S. Pat. No. 5,127,729 issued to Oetliker et al. discloses a light collector used in photometry having an elliptical reflector. An external light source illuminates a sample placed at one focus of the ellipse. A detector may be placed at the other focus. The sample is placed in a glass tube which is inserted through a hole in the elliptical reflector.

U.S. Pat. No. 5,216,479 issued to Dotan et al. discloses an optical inspection system used for inspecting the laminae of a printed circuit board (PCB). A laser beam is directed to the surface of the PCB. Specular and diffuse radiation is directed by a partial ellipsoidal reflector to filters and mirrors that reflect the radiation to detectors.

The DB100 Infrared Reflectometer, produced by the Gier Dunkle Instruments division of Dynatech Instruments, Inc., has an inspection head containing two rotating semi-cylindrical cavities. One of the cavities is heated by an electrical heater and the other stabilizes at approximately room temperature. Thus, the two cavities are maintained at different temperatures. As the cavities rotate, the sample is alternately irradiated. A vacuum thermocouple views the sample through an optical system that focuses through slits in the ends of the cavities. The detector receives energy emitted by the sample and energy reflected by the sample.

Of the above devices, only the DB100 Infrared Reflectometer is employed in a portable device for measuring the total reflectance (both diffuse and specular) properties of an arbitrary surface. The DB100 measures specular and partial (less than $2\pi$ steradian) diffuse reflectance and is limited in wavelength range by the deflector window. None of the above devices provide an absolute measurement of reflectance.

Thus, there exists a need for a device that measures both the total diffuse and specular reflectance properties of a surface.

There also exists a need for a device that measures the total reflectance properties of surfaces having arbitrary topography.

There also exists a need for a device that is easily calibrated to provide an absolute measurement of reflectance.

There also exists a need for a total reflectance measuring device that is portable.

There also exists a need for a coating for transducing light, especially infrared and visible light, into infrared light, which resists thermal shock and will not exhibit spalling or delamination when subjected to high temperatures.

SUMMARY OF THE INVENTION

The present invention is a device for measuring total specular and diffuse optical properties, such as reflectance, transmittance and emittance, from the surface of an object. It comprises a housing defining an ellipsoidal chamber having a reflective interior surface, a first focus and an opposite second focus. The chamber further defines a first aperture at the first focus which is adapted for placement against the surface of the object so that a portion of the surface is in optical communication with the chamber. A means is provided for illuminating the portion of the surface of the object through the first aperture with the electromagnetic radiation of a predetermined waveband, such as infrared. The illuminating means comprises a source of focused electromagnetic radiation.

When the first aperture is placed against the object, the electromagnetic radiation illuminates the object in an area at the first focus with the reflected radiation, both specular and scattered, being directed by the interior reflective surface to a means for measuring the reflected radiation.

Disposed between the first focus and the second focus is a means for reflecting substantially all of the electromagnetic radiation from the source of focused radiation to the radiation measuring means, thereby providing a reference beam to the radiation measuring means. The reflecting means comprises a mirror having a first end disposed outside the chamber, an opposite second end disposed inside the chamber, a reflective top surface and an opposite bottom surface with the mirror being movable between a first position and a second position. When the mirror is in the first position, a portion of the reflective top surface is disposed within the chamber, thereby reflecting substantially all of the electromagnetic radiation toward the second focus. When the mirror is in the second position, substantially all of the reflective top surface is disposed outside of the path of the electromagnetic radiation from the illuminating means, thereby allowing the focused electromagnetic radiation to illuminate the object unimpeded by the mirror.

In the preferred embodiment, the housing also defines a second aperture passing therethrough and the source of electromagnetic radiation is external to the chamber. The source of electromagnetic radiation comprises means for generating electromagnetic radiation of the predetermined waveband, means for focusing the electromagnetic radiation into a beam, and means for directing the beam through the second aperture onto the selected portion of the surface of the object.

To provide a signal compatible with the detector in the preferred embodiment and normal practices for electronic signal processing for optimum signal-to-noise ratios, means for periodically interrupting the beam of electromagnetic radiation are provided. Such interrupting means comprises a rotatable disk disposed between the source of electromagnetic radiation and the surface of the object and having an opening passing therethrough. The disk may have a plurality of openings angularly spaced evenly apart. A means is provided for rotating the disk at a predetermined period of rotation. The beam of electromagnetic radiation is directed so that the it passes through the disk opening for a portion of the period of rotation and is blocked by the disk for a portion of the period of rotation.

In one preferred embodiment, the housing comprises an aluminum ellipsoid having a polished interior surface. In an alternative preferred embodiment, the housing comprises two aluminum hemi-ellipsoids, each having a wide end, a more narrow end and a polished interior surface. The wide ends of the hemi-ellipsoids are in an abutting relationship with each other. This embodiment may be less costly to manufacture than the single ellipsoid embodiment.

The device may be embodied in a portable device. Such a device comprises a frame having a bottom side with the measuring device described above disposed so that the first aperture of the ellipsoidal reflector is adjacent the bottom side of the frame. In the portable embodiment, a means for holding the frame against the outer surface, such as a handle, is removably affixed to the frame.

The present invention also comprises a method for measuring total specular and diffuse reflectance from the surface of an object. To perform a measurement, an ellipsoidal reflector is placed against the surface of the object, the surface of the object is illuminated with a beam of electromagnetic radiation in the infrared range (however other wavebands may be used, depending on the application). The radiation reflected from the surface of the object, both specular and diffuse, is directed to a detector adjacent the second focus by the ellipsoidal reflector. Then the intensity of the reflected radiation is measured with the detector.

To provide an absolute measurement of reflectance, a base-line measurement is taken with each use. This is done by placing a reflector, having a reflectance substantially equal to the predetermined reflectance of the ellipsoidal reflector, in the beam of electromagnetic radiation so that substantially all of the electromagnetic radiation is diverted from the portion of the surface of the object to the detector. The radiation reflected from the reflector is measured and the base-line value of the measured radiation is stored. After measuring the light reflected off of the surface of the object, the absolute reflectance of the surface of the object is determined by dividing, with a calculating means, the value of the radiation reflected off of the object by the stored base-line value.

In yet another aspect, the present invention provides a coating for transducing a first light into infrared light comprising a composition made by the process of:

a. heating a mixture of a diphenyl siloxane polymer and a sufficient amount of carbon to absorb any oxygen present at a sufficiently high temperature for a sufficient time to pyrolyze and reduce the polymer to form a pigment, b. cooling the pigment to room temperature, c. grinding the pigment into granules, and d. mixing the granules with a binder and a liquid.

In another aspect, the present invention provides a coating for transducing a first light into infrared light comprising a carbon filled diphenyl siloxane polymer that has been pyrolyzed and reduced and a binder.

In another aspect, the invention provides a method of absorbing stray light or mediating radiation emittance comprising contacting said light or radiation with an electronic instrument, sensor or solar array that has been coated with the coating of the invention.

It is an object of the present invention to measure both the total diffuse and specular reflectance properties of a surface.

It is also an object of the present invention to determine an absolute measurement of reflectance.

It is also an object of the present invention to make a total reflectance measuring device portable so that reflectance measurements can be made without having to remove samples from the surfaces being measured.

These and other objects will become apparent from the following description of the preferred embodiments taken in conjunction with the following drawings, although variations and modifications may be effected without departing from the spirit and scope of the novel concepts of the disclosure.

BRIEF DESCRIPTION OF THE FIGURES OF THE DRAWINGS

FIG. 2a is a side elevational view of a portable embodiment of the present invention.

FIG. 2b is a front elevational view of the portable embodiment shown in FIG. 2a.

FIG. 4 is a front perspective view of the electrical and control unit.

FIG. 5a is a front elevational view of an ellipsoidal chamber used in a first alternative embodiment of the present invention used for taking angular measurements.

FIG. 5b is a front elevational view of an ellipsoidal chamber used in a second alternative embodiment of the present invention used for taking angular measurements.

FIG. 6a is a front elevational view of a first position of an ellipsoidal chamber used in a third alternative embodiment of the present invention.

FIG. 6a is a front elevational view of a second position of an ellipsoidal chamber used in a third alternative embodiment of the present invention.

FIG. 7 is a front elevational view of a fourth alternative embodiment of the present invention used to measure the diffuse component of reflected radiation.

DETAILED DESCRIPTION OF THE PREFERRED EMBODIMENTS

Figures 1A, 1B:
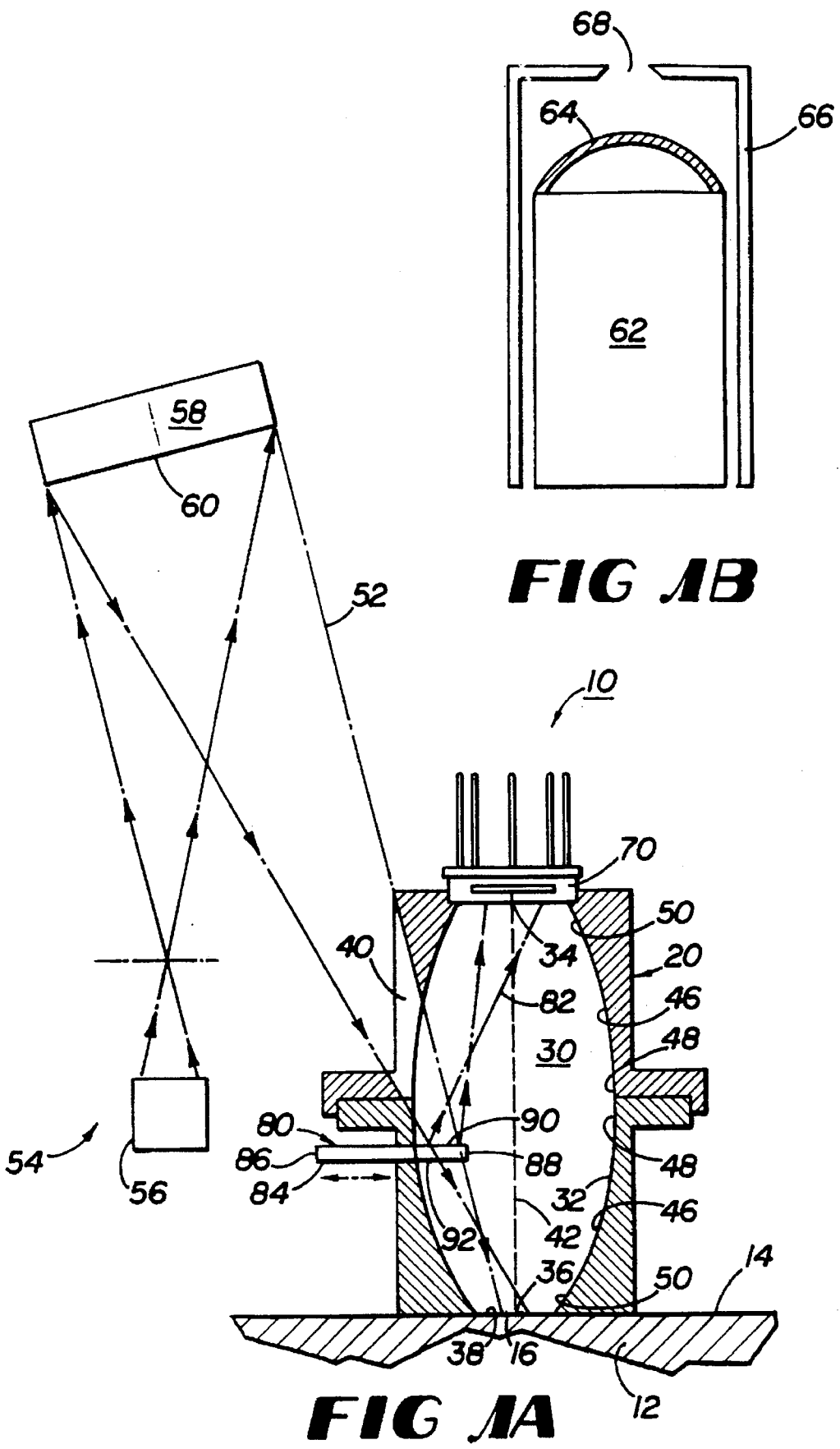
FIG. 1a is a side elevational view of the present invention.
FIG. 1b is a side schematic view of a radiation source used in the present invention.

The invention is now described in detail. Referring to the drawings, like numbers indicate like parts throughout the views.

Referring to FIG. 1a, the present invention 10 comprises a device for measuring the reflectance, emittance and transmittance of the surface 14 of an object 12. A housing 20 defines an ellipsoidal chamber 30 having a reflective interior surface 32. The ellipsoidal chamber 30 has a first focus 36 and a second focus 34, both disposed along a major axis 42. A first aperture 38 passes through the housing 20 at the first focus 36 so that when the first aperture 38 is placed against the surface 14 of the object 12, a portion 16 of the surface 14 is in optical communication with the ellipsoidal chamber 30. For ease of manufacture, the ellipsoidal chamber 30 can comprise two hemi-ellipsoids 46, each having a wide end 48 and a more narrow end 50, with the wide ends 48 in an abutting relationship and secured together by conventional means, such as adhesives or fasteners.

The housing 20 can be made of several materials. In one embodiment, the housing 20 comprises nickel with a gold-coated interior reflective surface 32. In another embodiment, the housing 20 comprises aluminum coated nickel. Furthermore, rather than polishing the interior surface 32 of the ellipsoidal chamber 30, the housing 20 may be electro-formed on a highly reflective mandrel (not shown).

An illuminating system 54, comprising a source 56 of electromagnetic radiation of a predetermined waveband and a means for focusing radiation (such as a lens or a curved mirror 58), generates a focused beam 52 of radiation. Typically, the waveband used in aerospace applications is in the infrared range, although other wavebands could be selected for other applications (e.g., if the present invention is used for colormetric analyses, the waveband corresponding to the colors typically absorbed by the surface being tested would be used).

As shown in FIG. 1b, the source 56 of electromagnetic radiation comprises a quartz lamp 62 coated with an infrared-emitting coating 64. The lamp 62 is encased in an opaque shroud 66 having an opening 68 through which infrared radiation escapes. One example of a suitable quartz lamp would be an L1030 or L1031 lamp from Gilway, Inc., of Woburn, Mass. The lamp is coated with a material that transduces light, preferably infrared and visible light, into completely infrared radiation. This material is prepared by subjecting a diphenyl siloxane polymer (such as DC808 silicone resin from Dow Corning, Inc.) to a highly reducing environment. To do so, the diphenyl siloxane polymer is placed in a stainless steel retort, or similar reaction vessel, along with sufficient carbon, such as, for example, a channel black or lamp black carbon, to absorb the oxygen present. The mixture is heated to a sufficiently high temperature for a sufficient time to pyrolyze and reduce the diphenyl siloxane polymer to form what is referred to as the pigment and what is believed to be, at least in part, a carbon filled glass matrix of silicon dioxide. In a preferred embodiment the polymer is heated at 900° C. for a period of four hours. The resulting composition is then allowed to cool to room temperature and is ground into granules, preferably having a mean diameter of about 25 microns. The granules are mixed with a binder, preferably a water-soluble amorphous material used as an inorganic binder, such as potassium silicate no. 2130 made by Philadelphia Quartz. In alternative embodiments, the binder can be lithium silicate, sodium silicate or mono-aluminum phosphate. A liquid, such as water, is also added to the pigment/binder mixture so that the mixture can be applied to a surface. In a preferred embodiment, the coating composition comprises 50 parts by weight of the pigment, 71.4 parts by/weight of the binder and 26.6 parts by weight water. Typically, the coating components are mixed for about one hour to achieve homogeneity. The coating is then sprayed, or otherwise deposited, onto the surface of the lamp 62. The coating is cured preferably for one day at room temperature at a humidity of from 30 to 70%. This coating is designed to meet the following requirements of the infrared source: it is highly absorptive of both visible and infrared light, it is highly transmissive of infrared light, it will resist thermal shock, and it will not exhibit spalling or delamination from the surface of the lamp 62 when subjected to high temperatures.

It should be noted that the above-described coating may also be used as a coating for electronic instrumentation, sensors and solar arrays used in spacecraft or other high temperature applications. For example, in a remote sensing satellite having a sensor array in which a narrow infrared cone angle is desired, this coating could be used to absorb stray light and may also be used as an emittance mediator. The coating can withstand high temperatures (up to 1500° C.

in a vacuum), and thus it is resistant to lasers, electromagnetic pulses and other threats. Furthermore, it has a low neutron cross section, thus allowing it to resist nuclear events. In such applications, the binder could be an organic compound, such as a suitable silicone.

Referring again to FIG. 1a, the focused beam 52 is directed through a second aperture 40 in the housing 20 toward the portion 16 of the surface 14 by a mirror 60. If a curved mirror is used as a focusing means 58, then one mirror 60 can perform both the focusing function and the directing function. The focused beam 52 impinges the surface 14 at an incident angle of about 15°.

A measuring means 70 is disposed perpendicular to the major axis 42 at the second focus 34. Virtually all (about 99%) of the electromagnetic radiation reflected off of the portion 16 of the surface 14, including both the specular and the diffuse components, is directed by the reflective interior surface 32 to the measuring means 70. Because both the specular component and the diffuse component of the reflected electromagnetic radiation are directed to the measuring means 70, the measuring means 70 must be sensitive enough to detect the diffusely scattered radiation directed to it, while being able to withstand the intensity of the specular component. A suitable windowless pyroelectric detector, coated for flat response through the far infrared, would meet both criteria. The detector should have a detectivity on the order of $10^8 D^*$ ($D^*$ being the reciprocal of Noise Equivalent Power). One such detector would be a P2-type detector from Molectron, Inc., of Portland, Oreg. This is a large-area detector (9 mm square) having uniform detectivity across its surface.

The overall size of the ellipsoidal chamber 30 is determined by the size of the measuring means 70, which must be large enough to intercept all of the reflected, transmitted, and emitted rays from the portion 16 of the surface 14. A large area detector of about 1 cm in diameter can be employed as a measuring means 70 in an ellipsoidal chamber 30 of about 5 cm height along the major axis 42. An array of ellipsoidal chambers can be used by using an array of detectors to increase the sampling area.

In order to achieve an "absolute" measurement of reflectance (i.e., one that is corrected for the transmissivity of the reflective interior surface 32), a reflecting means 80 is used to direct a reference 82 beam to the measuring means 70. The reflecting means 80 comprises a mirror 84 with a reflective top surface 90 having the same reflectance as the reflective interior surface 32 of the chamber 30, and an opposite bottom surface 92. The mirror 84 also has a first end 86 disposed outside the chamber 30 and an opposite second end 88 disposed inside the chamber 30. The mirror 84 is movable between a first position and a second position so that when the mirror 84 is in the first position, a portion of the reflective top surface 90 reflects substantially all of the focused beam 52 toward the second focus 34. When the mirror 84 is in the second position, substantially all of the reflective top surface 90 is disposed outside of the path of the focused beam 52, thereby allowing the focused beam 52 to illuminate the portion 16 of the surface 14 unimpeded by the mirror 84. A stepper motor (item 162 shown in FIG. 2b) is provided to move the mirror 84 between the first position and the second position at a predetermined rate.

The addition of the mirror 84 to intercept the focused beam 52 and direct it to the measuring means 70 allows a comparison of the input beam energy ($I_0$), as modified by the mirror reflectance ($R_{mirror}$), to the energy resulting when the mirror 84 is removed from the path of the beam 52 and $I_0$ is modified by the reflectance of the surface 14 ($R_{surf}$) and the reflectance of the ellipsoidal chamber 30 ($R_{ellips}$). Since the response of the measuring means 70 is the same for both cases, the resulting energy of the reference beam 82 reflected off of the reflective top surface 90 of the mirror 84 is given by $I_0 R_{mirror}$ and the resulting energy of the radiation reflected off of the surface 14 is given by $I_0 R_{surf} R_{ellips}$. If the reflective top surface 90 of the mirror 84 and the reflective interior surface 32 of the ellipsoidal chamber 30 are prepared similarly and from the same materials, their reflectances are the same, thus $R_{mirror}=R_{ellips}$. The reflectance of the surface 14 can then be calculated directly from the ratio of responses of the detector to the beam reflected from the mirror 82 and the surface 32:

$$R_{surf} = \frac{I_0 \cdot R_{surf} \cdot R_{ellips}}{I_0 \cdot R_{mirror}} = \frac{I_0 \cdot R_{surf} \cdot R_{mirror}}{I_0 \cdot R_{mirror}}$$

This measurement type tends to ratio out system errors and does not require the use of references or standards.

As shown in FIGS. 2a and 2b, the present invention may be embodied in a portable device 100 comprising a frame 102 having a bottom side 104. The housing 20 is disposed within the frame 102 with the first aperture 38 adjacent the bottom side 104.

Typically, an infrared source provides a beam with a temperature of about 220° C. To minimize non-gray sample measurement errors, the infrared source radiation should be modified to resemble a gray body curve at room temperature. A means for interrupting 120 the beam 52, disposed within the frame 102, modifies the beam so that it resembles such a gray body curve. The interrupting means 120 limits the mount of heat transferred to the surface being measured by limiting the amount of time the surface is exposed to the electromagnetic radiation. The interrupting means 120 provides a "chopped" or alternating beam to the surface and the measuring means is sensitive only to the chopped beam (as opposed to a continuous, or "DC," beam). This combination provides the advantage of making the present invention insensitive to ambient DC light. (However, prudent care to exclude ambient light should be used when taking measurements near pulsed light sources, such as fluorescent fixtures.)

The interrupting means 120 comprises a rotatable disk 122 having at least one opening 124 therethrough. A rotating means 126, such as an electric motor, is provided to rotate the disk 122 at a preselected rate. The opening 124 is aligned with the beam 52 so that the beam 52 is blocked by the disk 122 for a portion of the rotation cycle and passes through the opening 124 for a portion of the rotation cycle. A plurality of openings, evenly spaced around the disk 122, may be used to increase the frequency of chopping.

A handle 140 is removably attached to the frame 102 to provide a grip for the operator. The handle 140 is removable to facilitate storage and to allow the device 100 to be used in confined spaces.

A removable face plate 150 made of a highly reflective material, such as gold-plated aluminum or gold-plated nickel, is provided to stabilize the device 100 when used on flat or convex surfaces. The face plate 150 is removable to facilitate the use of the device 100 in measuring concave and other types of surfaces. The face plate 150 has a mating surface 154, shaped to receive the bottom side 104 of the frame 102, and a hole 152 that is aligned with the first aperture 38 when the face plate 150 is in use.

Figure 3:
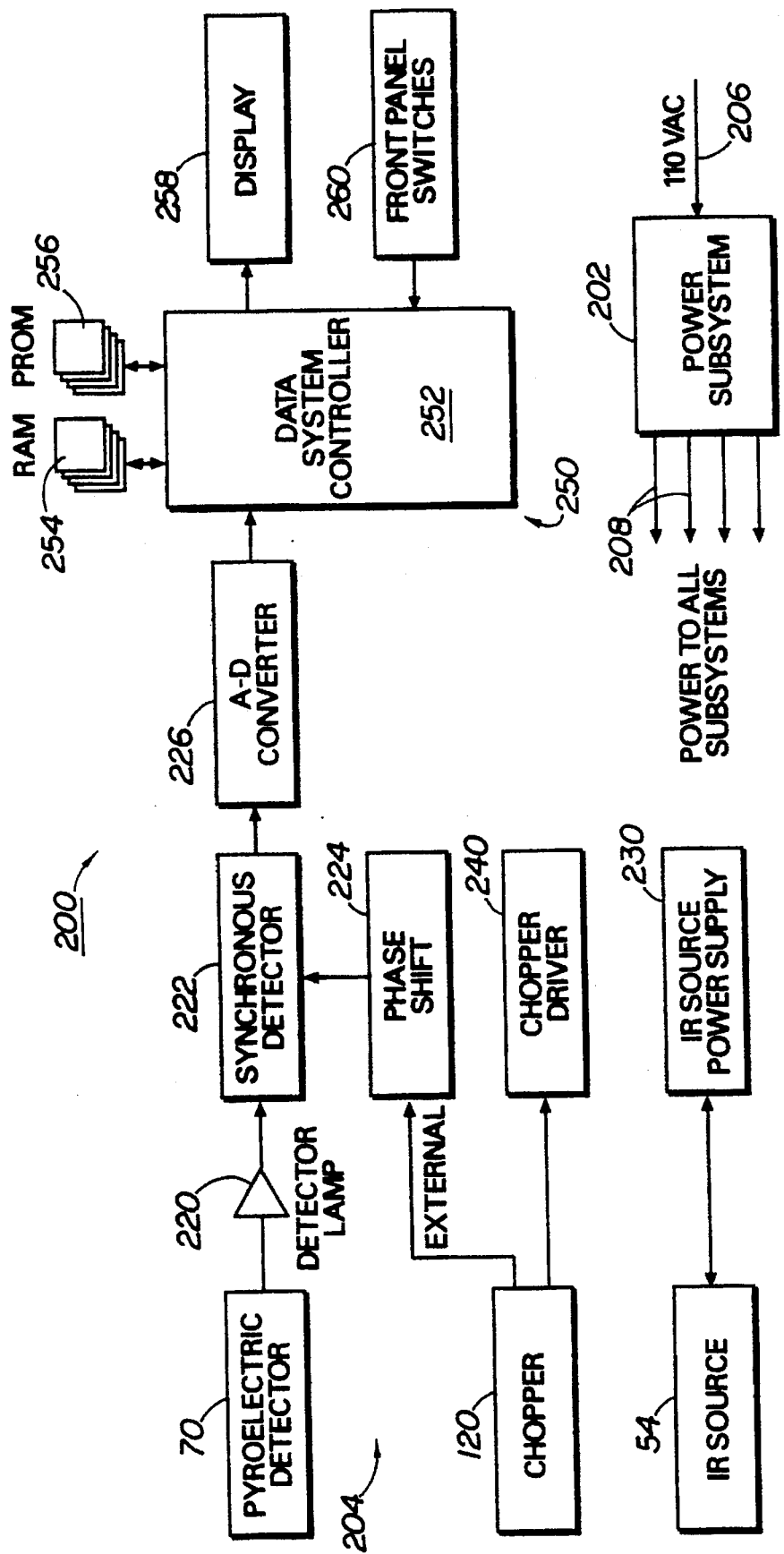
FIG. 3 is a schematic drawing of the electrical and control unit used in the present invention.

As shown in FIG. 3, the electrical and control unit 200 for the present invention comprises a power subsystem 202 and a control subsystem 204. The power subsystem 202, the design of which would be obvious to one skilled in the art of power system design, has a power input 206 from any conventional 120 VAC, 60 Hz, 0.25 amp power source and a plurality of power supply leads 208 supplying the necessary voltages to the components used in the device 100. For example, the electromagnetic radiation source 54 is supplied with a radiation source power supply lead 230 and the interrupting means 120 is supplied with power from the chopper driver lead 240.

The control subsystem 204 coordinates the measuring means 70 with the interrupting means 120 and provides properly conditioned signals to a calculating means 250 which calculates the reflectance of the surface being tested. The interrupting means 120 provides a coordinating signal, indicating when the beam is passing through the opening 124 in the disk 122, to a phase shifter 224. The phase shifter 224 synchronizes the signal with the period that the measuring means 70 would measure the reflected beam. The signal from the measuring means 70 is amplified by a preamplifier 220 and then fed into a frequency and phase sensitive synchronous detector 222, or lock-in amplifier, that accepts signal values from the preamplifier 220 only when the coordinating signal from the phase shifter 224 indicates that the measuring means 70 has measured a reflected beam. The output from the synchronous detector 222 is received by an analog-to-digital converter (ADC) 226 (such as a commonly available 12-bit ADC) that provides a digital signal representative of the intensity of the radiation measured by the measuring means 70 during the periods in which the interrupting means 120 allows radiation to pass onto the surface being tested.

The calculating means 250 comprises a data system controller 252 which could comprise one of many types of commonly available microprocessors. A random access memory (RAM) 254 and a programmable read only memory (PROM) 256 are both connected to the data system controller 252. Also connected to the data system controller 252 is a display output 258 and a plurality of panel switches 260 acting as control inputs. The data system controller 252, running a program stored in the PROM 256, stores the values of the base-line measurement and the total reflectance off of the surface in the RAM 254 and calculates the ratio of the total reflectance to the base-line measurement and displays the result on the display output 258.

Referring now to FIG. 4, the control unit 200 is housed in a control box 300 which comprises an enclosure 302 having a front panel 304 and a handle 306. Disposed on the front panel 304 is a display 310, preferably a liquid crystal display (LCD), and a plurality of front panel switches 320. The display 310 has a reflectance/emittance indicator 312 that indicates whether reflectance or emittance is being measured, a parameter value indicator 314 that indicates the value of reflectance or emittance being measured, and a mode indicator 316 that indicates whether absolute or relative measurements are being taken.

The front panel switches 320 include an on/off switch 322; a reflectance/emittance select switch 324, used to select between measuring reflectance and emittance; a mode select switch 326, used to select between a calibration mode, absolute mode or relative mode; and two calibration adjust switches 330. The calibration adjust switches 330 include a course switch 332 and a fine switch 334 both of which are used in calibrating the system.

In the preferred embodiment, the present invention determines total emittance by measuring total infrared reflectance. The emittance value for opaque materials is the complement of the reflectance and, therefore, is obtained by subtracting the reflectance value from unity. Either an emittance or a reflectance reading may be selected by selecting the appropriate position of the reflectance/emittance select switch 324.

If the operator desires to make relative measurements, the device must first be calibrated. This is done by moving the mode select switch 326 to the "calibrate" position. A sample of known high reflectance, such as a gold-plated disk (not shown), is placed over the first aperture (item 38 in FIGS. 1 & 2a and b) and the course switch 332 and the fine switch 334 are adjusted until the value on the parameter value indicator 314 corresponds to the known reflectance for the high reflectance sample. Next the mode switch 326 is depressed again and a sample of known low reflectance, such as a black disk (not shown), is placed over the first aperture 38 and the course switch 332 and the fine switch 334 are adjusted until the value on the parameter value indicator 314 corresponds to the reflectance for the low reflectance sample. The operator then changes the mode switch 326 from the "calibrate" to the "abs/rel" position, thereby causing the calibration values to be stored in the non-volatile memory 254 and selects the relative mode by pressing up on the mode switch 326 (which causes the mode to toggle between absolute and relative modes) until "rel" is displayed by the mode indicator 316. Measurements, relative to the calibration samples, may then be taken. It is not necessary to perform this calibration procedure when operating in the absolute mode.

The wavelength range is not limited by any windows, coatings or cut-off filters; thus, the measurement is performed over a wavelength range determined only by the physical laws governing the source emission ($\sigma \epsilon T^4$) and the detector's Noise Equivalent Power (NEP or 1/D*) characteristics, where $\sigma$ is the Stefan-Boltzman constant, $\epsilon$ is the emittance, and T is the temperature. A spectral range of less than 2.5 to more than 30 micrometers can be measured.

The invention provides total hemispheric measurements within a $2\pi$ steradian solid angle. These measurements are accomplished by providing near normal (about 15° from normal) incident energy to the sample surface and then collecting and measuring virtually all of the reflected energy, regardless of its degree of specularity or diffuseness.

The energy received by the detector is given by:

$$\epsilon_S \sigma T_S^4 + r_S \sigma T_{IR}^4 = I_D$$

where:

$\epsilon_S$=sample emittance
$\sigma$=Stefan-Boltzman constant
$T_S$=sample temperature (°K)
$r_S$=sample reflectance
$T_{IR}$=infrared source temperature (°K)
$I_D$=energy to the collector/detector system.

The first term radiates D.C. at ambient temperature, but since the detector does not respond to D.C., this term drops out. For this case, $T_{IR}$ is kept at a fixed value so that $\sigma T_{IR}^4$ becomes constant. In is thus only a function of $r_S$. If a known value of $r_S$ is used, the output meter response to $I_D$ can be adjusted to that value, e.g., 0.98 for gold reflectance. If the sample is removed from the aperture, both of the left hand terms drop out, since all the source energy exits the aperture ($r_S$=0). $I_D$ is thus zero, and the output meter can be so adjusted. Calibration to compensate for the effects of long term drift (tens of minutes) can be checked by measuring a gold sample and no sample or a gold sample and a black sample. In the absolute mode, reference samples and calibration procedures are unnecessary.

The present invention may also be used to approximate transmittance of the sample. To measure transmittance, a gold-plated disk is first placed behind the sample as a backing and the reflectance is measured. Next, a black disk is placed behind the sample and another reflectance measurement is taken. The transmittance is then determined by the following formula:

$$\tau_s \cong \sqrt{\frac{x - \rho_s}{\rho_{gold}}}$$

where:

$\tau_s$=transmittance of the sample;

$\rho_s$=reflectance of sample with black backing;

$\chi$=reflectance of the sample with gold backing; and $\rho_{gold}$=reflectance of the gold sample.

When measuring foil or wrinkled material, the material should be flattened over the measurement aperture with a heavier flat surface. This will ensure a relatively flat measurement surface.

Referring to FIGS. 5a & 5b, in an alternative embodiment, the present invention may also be adapted to measure angular optical properties of surfaces. To so adapt the present invention, an ellipsoidal chamber 430 having a plurality of apertures 420 passing therethrough is used. A detector 470 is disposed at one focus of the ellipsoidal chamber 430 and the ellipsoidal chamber 430 defines an aperture 438 at the opposite focus. The plurality of apertures 420 allows a focused beam (not shown) to enter the ellipsoidal chamber 430 so that it impinges the surface at various angles. In this embodiment, the source of radiation is movable relative to the ellipsoidal chamber 430 so that the focused beam can be directed through the various apertures. FIG. 5a shows an embodiment in which the apertures 420 are spaced apart parallel to the major axis, for taking measurements at various angles from the surface normal. FIG. 5b shows an embodiment in which a continuous slit 422 provides an entry path for taking measurements at all angles simultaneously, providing true total hemispherical measurement capability.

Referring to FIGS. 6a & 6b, in another alternative embodiment, absolute mode measurements may be taken without using a mirror to direct the beam 552 directly to the measuring means 570. In this embodiment, the baseline measurements are take by flipping the ellipsoidal chamber 530 180° about one of its minor axes 535 (the minor axes being those axes perpendicular to, and intersecting, the major axis at a point midway between the loci of the ellipse). The orientation of the ellipsoidal chamber 530 thus alternates between a first position, shown in FIG. 6a, and a second position, shown in FIG. 6b. The focused beam 552 directly illuminates the detector 570 through aperture 538 when the ellipsoid is in the first position, as shown in FIG. 6a. When the ellipsoidal chamber 530 is in the second position, the focused beam 552 passes through the second aperture 540 and illuminates the surface through the first aperture 538, as shown in FIG. 6b. In this case, as shown in FIG. 6a, the reflectance of the surface of the ellipsoidal chamber 530 is taken into account by reflecting the focused beam 552 off of the ellipsoidal chamber 530 prior to its reaching the measuring means 570, thereby giving a true absolute measurement.

FIG. 7 shows another alternative embodiment wherein the present invention may also be adapted to measure optical scatter from a surface. In this embodiment, an exit aperture 643 is provided on the side of the ellipsoidal chamber 630 opposite the first aperture 640. The focused beam 652 passes through the second aperture 640 and illuminates the surface through the first aperture 638. The exit aperture 643 is placed so that it allows the specular component 653 of the reflected beam out of the ellipsoidal chamber 630. Thus, the light directed to the detector 670 comprises only scattered light.

The above embodiments are given as illustrative examples and are not intended to impose any limitations on the invention. It will be readily appreciated that many deviations may be made from the specific embodiments disclosed in this specification without departing from the invention. Accordingly it is intended to cover all such modifications as within the scope of this invention.

What is claimed is:

1. A device for measuring total specular and diffuse optical properties from the surface of an object by means of electromagnetic radiation, comprising:

a. a housing defining an ellipsoidal chamber having a reflective interior surface, a first focus, an opposite second focus and the chamber defining a first aperture at the first focus, the first aperture being adapted for placement against the surface of the object so that a portion of the surface is in optical communication with the chamber;

b. means for illuminating the portion of the surface of the object with the electromagnetic radiation of a predetermined waveband; and c. means for measuring the radiation, disposed adjacent the second focus, so that when the first aperture is placed against the object, the electromagnetic radiation illuminates the object in an area adjacent the first focus with the reflected radiation, both specular and scattered, being directed by the reflective interior surface to the radiation measuring means.

2. The device of claim 1, wherein the predetermined waveband of electromagnetic radiation is in the infrared range.

3. The device of claim 1, wherein the predetermined waveband of electromagnetic radiation is in the near-infrared range.

4. The device of claim 1, wherein the predetermined waveband of electromagnetic radiation is in the visible range.

5. The device of claim 1, wherein the predetermined waveband of electromagnetic radiation is in the ultraviolet range.

6. The device of claim 1, wherein the illuminating means comprises a source of focused electromagnetic radiation of the predetermined waveband.

7. The device of claim 6 wherein the source of focused electromagnetic radiation comprises a lamp having a surface coated with a material that absorbs light emitted by the lamp and emits electromagnetic radiation of the predetermined waveband.

8. The device of claim 6 further comprising means, disposed between the first focus and the second focus, for reflecting substantially all of the electromagnetic radiation from the source of focused radiation to the radiation measuring means, thereby providing a reference beam to the radiation measuring means.

9. The device of claim 8 wherein the reflecting means comprises:

a. a mirror having a first end disposed outside the chamber, an opposite second end disposed inside the chamber, a reflective top surface and an opposite bottom surface, the mirror being movable between a first position and a second position; and b. means for moving the mirror between the first position and the second position, so that when the mirror is in the first position, a portion of the reflective top surface is disposed within the chamber thereby reflecting substantially all of the electromagnetic radiation toward the second focus and when the mirror is in the second position, substantially all of the reflective top surface is disposed outside of the path of the electromagnetic radiation from the illuminating means, thereby allowing the focused electromagnetic radiation to illuminate the object unimpeded by the mirror.

10. The device of claim 6, wherein the housing defines a second aperture passing therethrough and wherein the source of electromagnetic radiation is external to the chamber and comprises:

a. means for generating electromagnetic radiation of the predetermined waveband;

b. means for focusing the electromagnetic radiation into a beam; and c. means for directing the beam through the second aperture onto the portion of the surface of the object.

11. The device of claim 10 further comprising means for periodically interrupting the beam of electromagnetic radiation.

12. The device of claim 11 wherein the interrupting means comprises:

a. a rotatable disk disposed between the source of electromagnetic radiation and the surface of the object and having an opening passing therethrough; and b. means for rotating the disk at a predetermined period of rotation, the beam of electromagnetic radiation directed so that the beam of electromagnetic radiation passes through the opening for a portion of the period of rotation and is blocked by the disk for a portion of the period of rotation.

13. The device of claim 1, wherein the housing comprises an aluminum ellipsoid having a polished interior surface.

14. The device of claim 1, wherein the housing comprises gold coated nickel.

15. The device of claim 1, wherein the housing comprises aluminum coated nickel.

16. The device of claim 1, wherein the housing comprises two hemi-ellipsoids each having a wide end, a more narrow end and a polished interior surface, the wide ends of the hemi-ellipsoids in an abutting relationship with each other.

17. A portable device for measuring the total specular and diffuse reflectance from a surface of an object, comprising:

a. a frame having a bottom side;

b. a housing disposed within the frame and defining an ellipsoidal reflector, the reflector comprising a reflective inside surface, a major axis, a first focus and an opposite second focus disposed along the major axis, the reflector truncated by a plane perpendicular to the major axis at the first focus and defining an aperture therethrough, the reflector disposed so that the aperture is adjacent the bottom side of the frame so that when the bottom side of the frame is placed against the surface of the object, a portion of the surface is adjacent the first focus and in optical communication with the inside of the reflector;

c. means, disposed within the frame, for illuminating a portion of the surface with electromagnetic radiation having a predetermined wave band;

d. means for directing the beam to the portion of the outer surface; and e. means, disposed along a plane perpendicular to the major axis at the second focus, for measuring the intensity of the reflected electromagnetic radiation reflected off of the portion of the surface and for generating a signal representative of the measured intensity.

18. The device of claim 17 wherein the illuminating means comprises:

a. means, disposed within the frame, for generating a beam of light within the predetermined waveband;

b. means for directing the beam onto the surface portion of the object; and c. means for limiting the mount of heat transferred from the beam to the object.

19. The device of claim 18 wherein the limiting means comprises means, disposed between the beam generating means and the portion of the outer surface, for periodically interrupting the beam.

20. The device of claim 19 wherein the interrupting means comprises:

a. a rotatable disk, disposed between the source of electromagnetic radiation and the surface of the object, having an opening passing therethrough; and b. means for rotating the disk at a predetermined period of rotation, the beam of electromagnetic radiation directed so that the beam of electromagnetic radiation passes through the opening for a portion of the period of rotation and is blocked by the disk for a portion of the period of rotation.

21. The device of claim 17 wherein the beam generating means is disposed outside the housing and the housing has a second aperture passing therethrough adapted to allow passage of the beam onto the portion of the outer surface.

22. The device of claim 17 further comprising means, disposed between the first focus and the second focus, for reflecting substantially all of the electromagnetic radiation from the source of focused radiation to the radiation measuring means, thereby providing a reference beam to the radiation measuring means.

23. The device of claim 22 wherein the reflecting means comprises:

a. a mirror having a first end disposed outside the chamber, an opposite second end disposed inside the chamber, a reflective top surface and an opposite bottom surface, the mirror being movable between a first position and a second position; and b. means for moving the mirror between the first position and the second position, so that when the mirror is in the first position, a portion of the reflective top surface is disposed within the chamber thereby reflecting substantially all of the electromagnetic radiation toward the second focus and so that when the mirror is in the second position, substantially all of the reflective top surface is disposed outside of the path of the electromagnetic radiation from the illuminating means, thereby allowing the focused electromagnetic radiation to illuminate the object unimpeded by the mirror.

24. The device of claim 23 further comprising calculation means, responsive to the signal representative of the measured intensity, for determining the absolute total hemispheric reflectance of the portion of the surface by calculating the ratio of the measured intensity of the reflected beam when the mirror is in the second position divided by the measured intensity of the reflected beam when the mirror is in the first position.

25. The device of claim 17 further comprising means for holding the frame against the outer surface.

26. The device of claim 25 wherein the holding means comprises a handle removably affixed to the frame.

27. The device of claim 17 further comprising a plate, removably attached to the bottom side of the frame and defining a hole in alignment with the first aperture, comprising a highly reflective material for stabilizing the device when used on non-concave surfaces.

28. The device of claim 17 wherein the housing defines a plurality of spaced apart apertures and the illuminating means is moveable relative to the housing to allow the measurement of angular optical properties.

29. The device of claim 28 wherein the plurality of spaced apart apertures are defined along a line parallel to the major axis of the ellipsoidal chamber.

30. The device of claim 28 wherein the plurality of spaced apart apertures are defined along a line perpendicular to the major axis of the ellipsoidal chamber.

31. The device of claim 17 wherein the housing is rotatable around a minor axis of the ellipsoidal chamber, the housing having a first position and a second position and wherein the housing defines a third aperture, so that when the housing is in the first position, the beam is directed through the third aperture to the measuring means, and so that when the housing is in the second position, the beam is directed through the first aperture.

32. The device of claim 17 wherein the reflected beam has a diffuse component and a specular component, and wherein the housing defines an exit aperture, the exit aperture being disposed so that the specular component of the reflected beam exits through the exit aperture, thereby allowing the device to perform measurements of the optical scatter properties of a surface.

33. A method for measuring total specular and diffuse reflectance from the surface of an object, comprising the steps of:

a. placing against the surface of the object an ellipsoidal reflector, having a reflective interior surface, a first focus, an opposite second focus and defining a first aperture at the first focus, the first aperture being adapted for placement against the surface of the object;

b. illuminating, with a beam of electromagnetic radiation of a predetermined waveband, a portion of the surface through an aperture in the ellipsoidal reflector;

c. reflecting, with the ellipsoidal reflector, a portion of the electromagnetic radiation reflected from the surface of the object, both specular and diffuse, to a detector adjacent the second focus; and d. measuring a value of the reflected radiation with the detector.

34. The method of claim 33, wherein the predetermined waveband of electromagnetic radiation is in the infrared range.

35. The method of claim 33, wherein the predetermined waveband of electromagnetic radiation is in the near-infrared range.

36. The method of claim 33, wherein the predetermined waveband of electromagnetic radiation is in the visible range.

37. The method of claim 33, wherein the predetermined waveband of electromagnetic radiation is in the ultraviolet range.

38. The method of claim 33 further comprising the step of taking a base-line measurement with the measurement instrument to achieve an absolute measurement of reflectance.

39. The method of claim 38 wherein the base-line measuring step comprises the steps of:

a. placing a reflector, having a reflectance substantially equal to the predetermined reflectance of the ellipsoidal reflector, in the beam of electromagnetic radiation so that substantially all of the electromagnetic radiation is diverted from the portion of the surface of the object to detector;

b. measuring the radiation reflected from the reflector; and c. storing a value of the measured base-line radiation.

40. The method of claim 39 further comprising determining the reflectance of the surface of the object by dividing the value of the radiation reflected off of the object by the value of the stored base-line radiation reflected from the reflector.

* * * * *